United States Patent [19]
Wright

[11] Patent Number: 5,846,193
[45] Date of Patent: Dec. 8, 1998

[54] MIDCAB RETRACTOR

[76] Inventor: John T. M. Wright, 555 S. Downing St., Denver, Colo. 80209

[21] Appl. No.: 850,317

[22] Filed: May 1, 1997

[51] Int. Cl.⁶ .................................................. A61B 17/02
[52] U.S. Cl. .......................... 600/215; 600/222; 600/232
[58] Field of Search ................................... 600/214, 215, 600/216, 222, 225, 232

[56] References Cited

U.S. PATENT DOCUMENTS

| | | | |
|---|---|---|---|
| 1,401,190 | 12/1921 | Risley | 600/215 |
| 2,751,903 | 6/1956 | Ivory et al. | 600/216 |
| 4,239,036 | 12/1980 | Krieger | 600/216 |
| 4,263,899 | 4/1981 | Burgin | 600/222 |
| 4,726,356 | 2/1988 | Santilli | 600/232 |
| 4,829,985 | 5/1989 | Couetil | 600/232 |
| 5,052,373 | 10/1991 | Michelson | 600/232 |
| 5,067,477 | 11/1991 | Santangelo | 600/222 |
| 5,616,117 | 4/1997 | Dinkler et al. | 600/215 |

*Primary Examiner*—Paul J. Hirsch

[57] ABSTRACT

An improved surgical retractor of the type that comprises a rack and pinion for moving an arm mount which supports the pinion and is moved when the pinion is turned, a hinge connecting the mount to an arm and a blade mount and a fixed arm mounted on the other end of the rack, a hinge connecting the mount to an arm and a blade mount wherein the improvement comprises a pair of opposed blade assemblies mounted on the respective blade mounts, said blade assemblies being so configured and constructed as to permit the respective blades to pivot independently of the blade mount and to be locked at an angle relative to each other and to the rack, is disclosed.

2 Claims, 2 Drawing Sheets

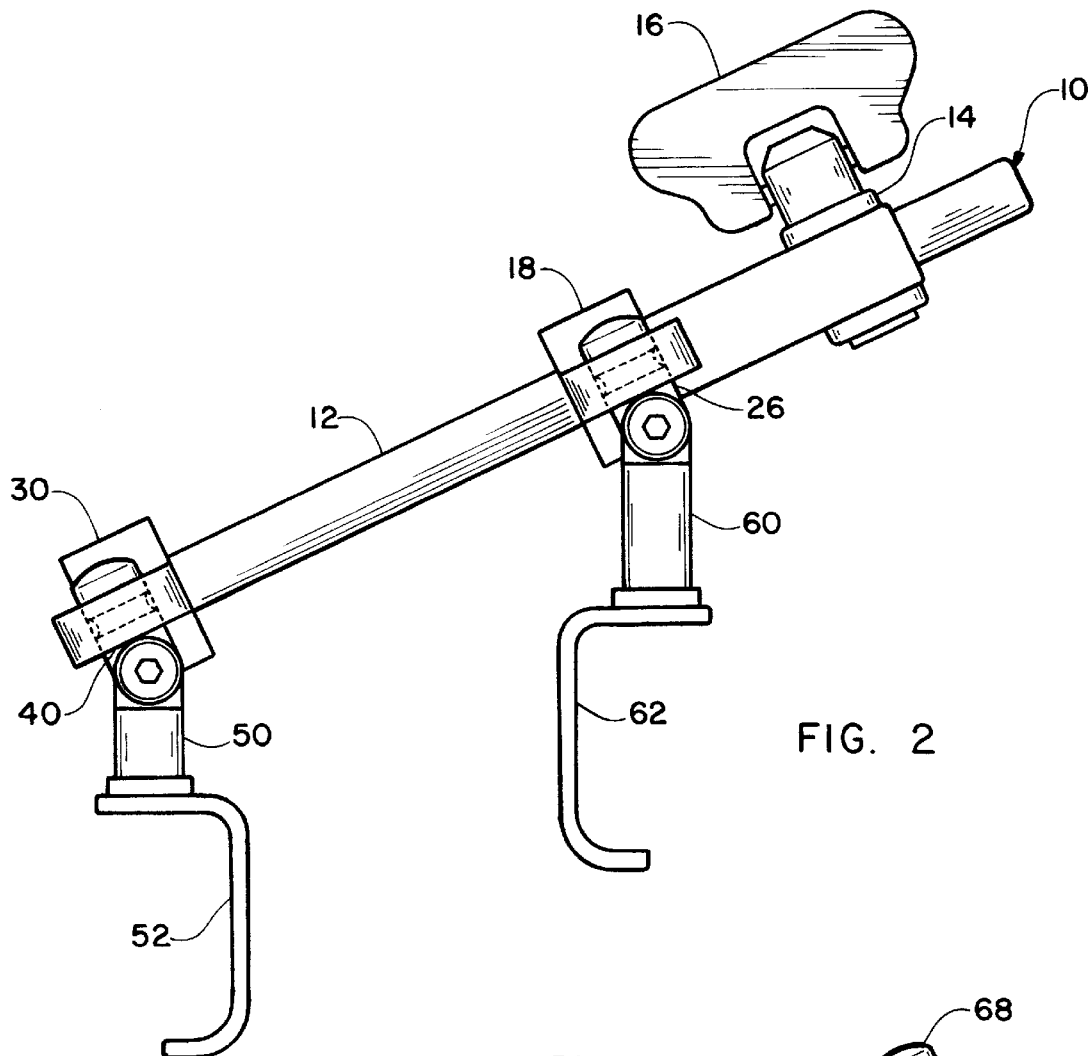
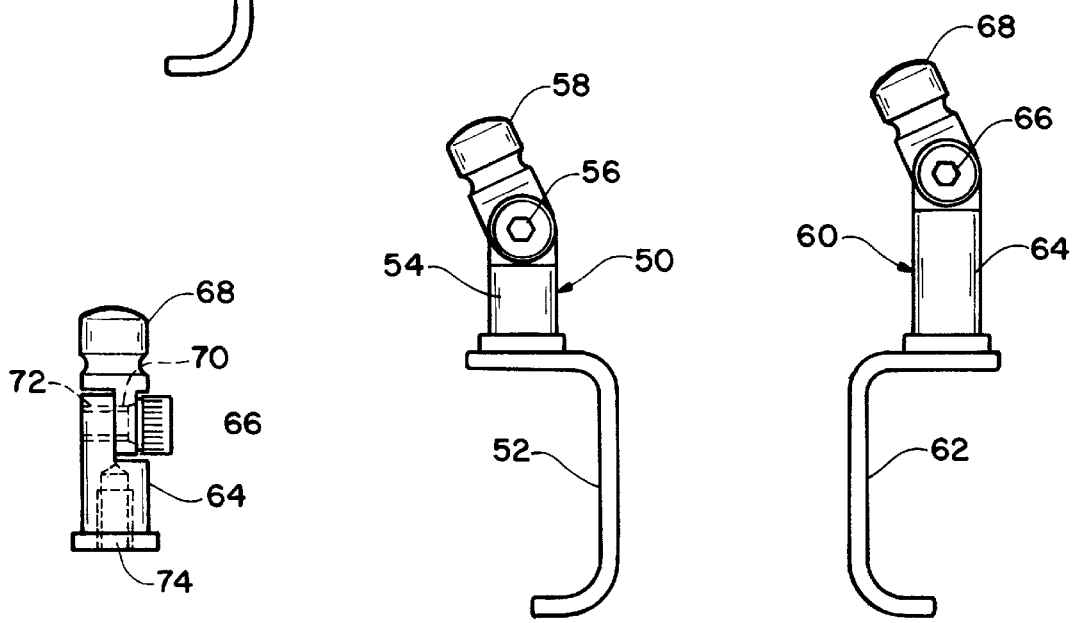
FIG. 2
FIG. 5   FIG. 3   FIG. 4

MIDCAB RETRACTOR

FIELD OF THE INVENTION

This invention relates to surgical devices and specifically to retractors suitable for use in Minimally Invasive Direct Coronary Artery Bypass surgical techniques, and for other minimally invasive surgical procedures.

BACKGROUND OF THE INVENTION

In Minimally Invasive Direct Coronary Artery Bypass (MIDCAB) surgery, it is important that part of the sternum or upper ribs be raised relative to the opposing side of the wound so that the internal mammary artery may be freed and made available to be anastomosed to the diseased coronary artery.

SUMMARY OF THE INVENTION

A specially improved retractor, based on a known rack and pinion type of retractor supplied by Pacific surgical Innovations, Inc. which uses plug in blades is described and claimed in this patent application.

The essence of the invention is the incorporation of adjustable and locking hinges into the blade plugs.

BRIEF DESCRIPTION OF THE DRAWINGS

FIG. 2 is a view of the improved retractor of this invention showing the vertical configuration of the retractor as it would appear in use.

FIGS. 3 and 4 depict alternative embodiments of the blade assemblies of the invention.

FIG. 5 is a side elevational view of a typical blade hinge assembly.

DESCRIPTION OF THE PREFERRED EMBODIMENTS

Figure 1:
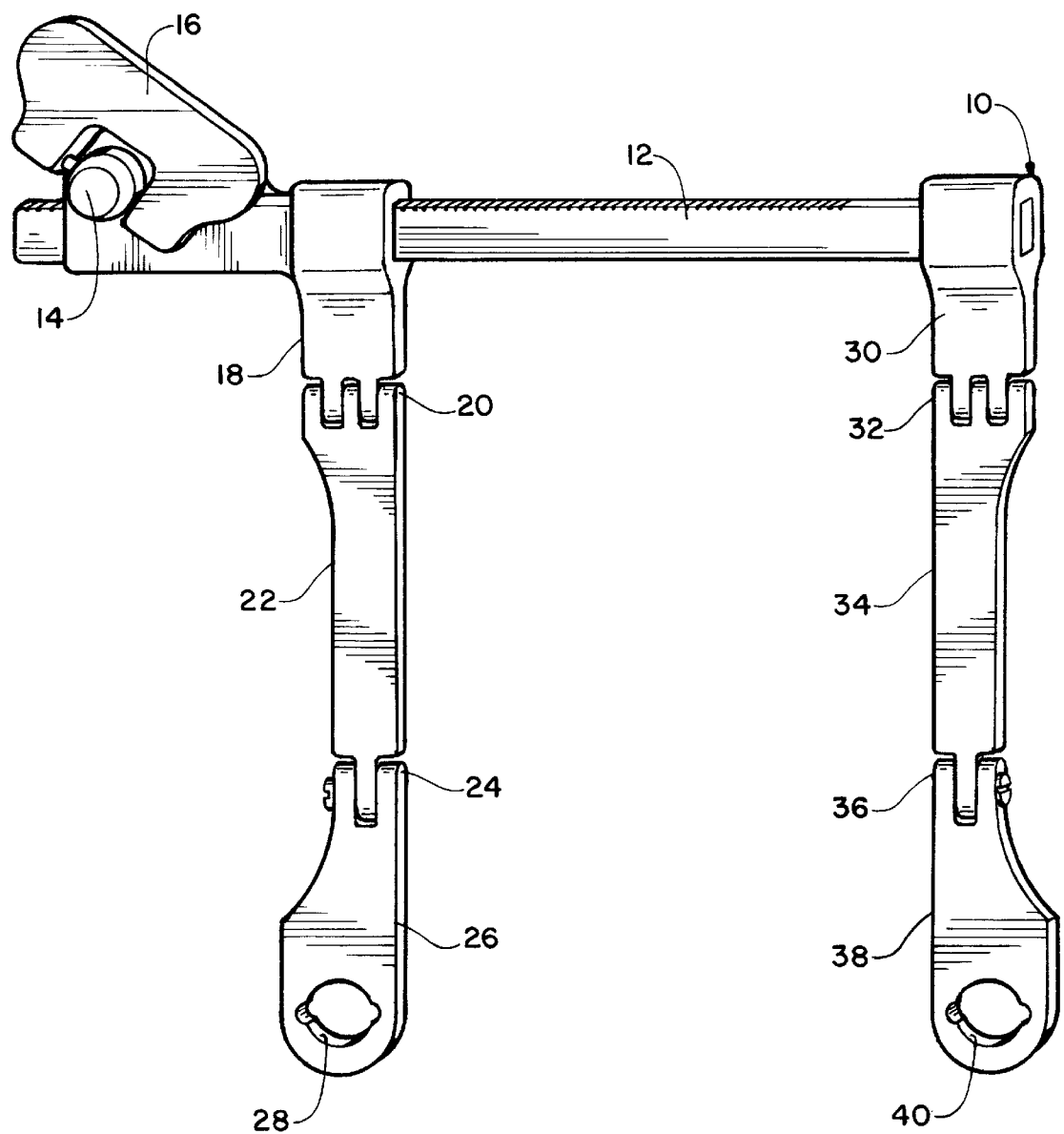
FIG. 1 is a top plan view, shown in perspective, of the basic prior art rack and pinion retractor which may be improved to provide the present invention. Other retractors may be used, the illustrated retractor being merely exemplary.

The prior art retractor shown in FIG. 1 is exemplary of a simple rack and pinion retractor that may used as a convenient starting point in the manufacture of the present invention. Other known or specially designed retractors may, however, be used equally well.

The basic exemplary retractor 10 comprise a rack 12 and pinion 14 operable by a twist handle 16 for moving one arm mount 18, which supports the pinion and is moved when the pinion is turned, which in one embodiment comprises a hinge 20 connecting the mount 18 to an arm 22 which, in turn, may comprise another hinge 24 supporting a blade mount 26. The blade mount may use any mechanism for permitting securement to the mount, a modified bayonet type aperture 28 being shown. A fixed arm 30 is mounted on the other end of the rack. Components 32, 34, 36, 38 and 40 correspond in a mirror image fashion to components 20, 22, 24, 26 and 28, respectively.

The improvement of this invention is the inclusion in a retractor generally as described of a pair of opposed blade assemblies 50 and 60 that are so configured and constructed as to permit the respective blades to pivot independently of the blade mount and to be locked at an angle relative to each other and to the rack as may determined by the surgeon. The blade assembly 50 comprises a blade 52, a mounting post 54, a lockable pivot assembly 56 and means 58 for being secured to the blade mount of the retractor. The blade assembly 60 comprises a blade 62, a mounting post 64, a lockable pivot assembly 66 and means 68 for being secured to the blade mount of the retractor. The mounting post 64 is longer than the mounting post 54. In practice, the mounting posts may be the same length or any of several different lengths.

In use, the surgeon loosens the locking socket screws, adjusts the angle of the blades as appropriate, say to 30 degrees, and re-locks the screws. When the blades are placed into the incision and the retractor is cranked open the upper blade will be lifted as will be the upper portion of the incision. Depending upon the patients anatomy an external force may have to be applied by, say, a surgical assistant. Using a prior art attachment block on one arm of the retractor a pillar clamp, mounting bar and ball clamp may be mounted as described in U.S. patent application Ser. No. 08/518,035 now U.S. Pat No. 5,653,741. The cardiac stabilizer surgical device may then be attached in turn to the retractor using the ball clamp described in said application.

The same type of retractor, but without the lockable hinged blades, may also be used for a minimally invasive mitral valve retractor. Hence one benefit of the invention is that a single retractor may be used for different operation by using the alternative plug in blades.

Industrial Application

This invention is useful in the surgical appliance industry and in the practice of surgery on human and animal subjects.

What is claimed is:

1. In a surgical retractor that comprises a rack (12) and pinion (14) for moving an arm mount (18) which supports the pinion and is moved when the pinion is turned, a hinge (20) connecting the mount (18) to an arm (22) and a blade mount (26) and a fixed arm (30) mounted on the other end of the rack, a hinge (32) connecting the mount (30) to an arm (34) and a blade mount (38), the improvement further comprising a pair of opposed blade assemblies (50) and (60) mounted on the respective blade mounts, said blade assemblies, respectively, comprising a blade, a mounting post, a lockable pivot assembly and means for being secured to the blade mount of the retractor, and being so configured and constructed as to permit the respective blades to pivot independently of the blade mount and to be locked at an angle relative to each other and to the rack.

2. A surgical retractor system comprising a moveable arm, a rack having two ends and a pinion for moving the moveable arm, the pinion being mounted in the moveable arm configured and constructed to be moved when the pinion is turned, a blade mount connected to the moveable arm by a hinge, a fixed arm mounted on an end of the rack, a blade mount connected to the fixed arm by a hinge, said blade mounts, respectively, comprising a mounting post, a lockable pivot assembly, means for securing the blade mounts to the respective arms, and means for mounting a blade on the blade mounts, the system being so configured and constructed as to permit interchangeable blades mounted on the respective blade mounts to pivot independently of the blade mount and to be locked at an angle relative to each other and to the rack.

* * * * *